(12) United States Patent
Lai et al.

(10) Patent No.: US 8,080,234 B2
(45) Date of Patent: *Dec. 20, 2011

(54) PROCESS FOR MANUFACTURING MCM-22 FAMILY MOLECULAR SIEVES

(75) Inventors: Wenyih Frank Lai, Bridgewater, NJ (US); Robert Ellis Kay, Easton, PA (US)

(73) Assignee: ExxonMobil Chemical Patents, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/856,098

(22) Filed: Aug. 13, 2010

(65) Prior Publication Data

US 2011/0021855 A1 Jan. 27, 2011

Related U.S. Application Data

(62) Division of application No. 11/657,315, filed on Jan. 24, 2007, now Pat. No. 7,799,316.

(60) Provisional application No. 60/773,135, filed on Feb. 14, 2006.

(51) Int. Cl.
  *C01B 39/46* (2006.01)
(52) U.S. Cl. .......... 423/718; 423/702; 423/706; 208/46; 208/111.01; 208/135
(58) Field of Classification Search .................. 423/702, 423/706, 718; 208/46, 111.01, 135
See application file for complete search history.

(56) References Cited

U.S. PATENT DOCUMENTS

| | | | |
|---|---|---|---|
| 4,100,262 A | 7/1978 | Pelrine | |
| 4,439,409 A | 3/1984 | Puppe et al. | |
| 4,721,806 A | 1/1988 | Zinnen | |
| 4,721,807 A | 1/1988 | Zinnen | |
| 4,826,667 A | 5/1989 | Zones et al. | |
| 4,873,067 A | 10/1989 | Valyocsik et al. | |
| 4,954,325 A | 9/1990 | Rubin et al. | |
| 4,954,663 A | 9/1990 | Marler et al. | |
| 4,956,514 A | 9/1990 | Chu | |
| 4,956,663 A | 9/1990 | Gerstch | |

(Continued)

FOREIGN PATENT DOCUMENTS

CN 1 296 913 5/2001

(Continued)

OTHER PUBLICATIONS

Baerlocher et al., "Atlas of Zeolite Framework Types," Fifth Ed., 2001.

(Continued)

*Primary Examiner* — David M Brunsman
(74) *Attorney, Agent, or Firm* — D.M. Tyus

(57) ABSTRACT

A method of manufacturing a molecular sieve of the MCM-22 family, said method comprising the steps of (a) providing a mixture comprising at least one source of ions of tetravalent element, at least one source of alkali metal hydroxide, at least one directing-agent (R), water, and optionally at least one source of ions of trivalent element, said mixture having the following mole composition:

$Y:X_2 = 10$ to infinity
$H_2O:Y = 1$ to 20
$OH^-:Y = 0.001$ to 2
$M^+:Y = 0.001$ to 2
$R:Y = 0.001$ to 0.34 wherein Y is a tetravalent element, X is a trivalent element, M is an alkali metal; (b) treating said mixture at crystallization conditions for less than 72 hr to form a treated mixture having said molecular sieve, wherein said crystallization conditions comprise a temperature in the range of from about 160° C. to about 250° C.; and (c) recovering said molecular sieve.

8 Claims, 3 Drawing Sheets

U.S. PATENT DOCUMENTS

| | | | |
|---|---|---|---|
| 4,962,239 A | 10/1990 | Bell et al. | |
| 4,962,250 A | 10/1990 | Dessau et al. | |
| 4,962,256 A | 10/1990 | Le et al. | |
| 4,962,257 A | 10/1990 | Absil et al. | |
| 4,968,402 A | 11/1990 | Kirker et al. | |
| 4,973,781 A | 11/1990 | Valyocsik et al. | |
| 4,973,784 A | 11/1990 | Han et al. | |
| 4,982,033 A | 1/1991 | Chu et al. | |
| 4,982,040 A | 1/1991 | Angevine et al. | |
| 4,983,276 A | 1/1991 | Absil et al. | |
| 4,986,894 A | 1/1991 | Keville et al. | |
| 4,992,606 A | 2/1991 | Kushnerick et al. | |
| 4,992,611 A | 2/1991 | Morrison | |
| 4,992,615 A | 2/1991 | Huss, Jr. et al. | |
| 5,000,839 A | 3/1991 | Kirker et al. | |
| 5,001,283 A | 3/1991 | Altman et al. | |
| 5,001,295 A | 3/1991 | Angevine et al. | |
| 5,001,296 A | 3/1991 | Howley et al. | |
| 5,012,033 A | 4/1991 | Child et al. | |
| 5,013,422 A | 5/1991 | Absil et al. | |
| 5,019,664 A | 5/1991 | Del Rossi et al. | |
| 5,019,665 A | 5/1991 | Partridge et al. | |
| 5,019,670 A | 5/1991 | Le et al. | |
| 5,143,879 A | 9/1992 | Whitehurst | |
| 5,164,170 A | 11/1992 | Rubin | |
| 5,236,575 A | 8/1993 | Bennett et al. | |
| 5,240,892 A | 8/1993 | Klocke | |
| 5,250,277 A | 10/1993 | Kresge et al. | |
| 5,362,697 A | 11/1994 | Fung et al. | |
| 5,558,851 A | 9/1996 | Miller | |
| 5,871,650 A | 2/1999 | Lai et al. | |
| 5,895,769 A | 4/1999 | Lai | |
| 5,925,330 A | 7/1999 | Roth | |
| 6,077,498 A | 6/2000 | Diaz Cabanas et al. | |
| 6,099,820 A | 8/2000 | Miller | |
| 6,342,200 B1 | 1/2002 | Rouleau et al. | |
| 6,936,744 B1 | 8/2005 | Cheng et al. | |
| 7,011,810 B2 | 3/2006 | Dakka et al. | |
| 7,799,316 B2* | 9/2010 | Lai et al. | 423/706 |
| 7,816,573 B2 | 10/2010 | Lai et al. | |
| 7,829,062 B2* | 11/2010 | Lai et al. | 423/700 |
| 7,842,277 B2* | 11/2010 | Roth et al. | 423/718 |
| 7,846,418 B2* | 12/2010 | Lai et al. | 423/718 |
| 8,017,540 B2 | 9/2011 | Lai et al. | |
| 2004/0030212 A1 | 2/2004 | Al-Soufi et al. | |
| 2007/0191660 A1 | 8/2007 | Johnson et al. | |
| 2007/0191663 A1 | 8/2007 | Johnson et al. | |
| 2010/0147741 A1 | 6/2010 | Lai et al. | |

FOREIGN PATENT DOCUMENTS

| | | |
|---|---|---|
| CN | 1699170 A | 11/2005 |
| DE | 3625693 | 2/1988 |
| EP | 0 174 121 | 3/1986 |
| EP | 0 284 206 | 9/1988 |
| EP | 0 293 032 | 11/1988 |
| EP | 0 999 182 | 5/2000 |
| EP | 1 105 348 | 3/2001 |
| EP | 1 249 428 | 10/2002 |
| EP | 1 061 046 | 9/2007 |
| WO | WO 92/12928 | 8/1992 |
| WO | WO 96/01687 | 1/1996 |
| WO | WO 97/17290 | 5/1997 |
| WO | WO 00/06494 | 2/2000 |
| WO | WO 03/006160 | 1/2003 |
| WO | WO 03/006405 | 1/2003 |
| WO | WO 03/029144 | 4/2003 |
| WO | WO 03/093230 | 11/2003 |
| WO | WO 2004/052810 | 6/2004 |
| WO | WO 2005/118476 | 12/2005 |
| WO | WO 2006/015824 | 2/2006 |
| WO | WO 2006/015825 | 2/2006 |
| WO | WO 2006/015826 | 2/2006 |
| WO | WO 2007/094949 | 8/2007 |

OTHER PUBLICATIONS

Corma et al., "Synthesis and characterization of the MCM-22 zeolite", Zeolite 15 (1995), pp. 2-8.

Guray et al., "Synthesis of Zeolite MCM-22 Under Rotating and Static Conditions", Microporous and Mesoporous Materials 31 (1999), pp. 241-251.

Inagaki et al., "Textural and Catalytic Properties of MCM-22 Zeolite Crystallized by the Vapor-Phase Transport Method," Bull. Chem. Soc. Jpn., 77 (2004), pp. 1249-1254.

Kim et al., "Synthesis of Zeolites by Water-Organic Vapor-Phase Transport," Microporous Materials, 1 (1993), pp. 191-200.

Lok et al., "The Role of Organic Molecules in Molecular Sieve Synthesis," Zeolites, vol. 3, Oct. 1983, pp. 282-291.

Matsukata et al., "Synthesis of Zeolites Under Vapor Atmosphere, Effect of Synthetic Conditions on Zeolite Structure," Microporous Materials, 1 (1993), pp. 219-222.

Mochida et al., "The Effects of Seeding in the Synthesis of Zeolite MCM-22 in the Presence of Hexamethyleneimine," Zeolites 18 (1997), pp. 142-151.

Ravishankar et al., "Characterization and Catalytic Properties of Zeolite MCM-22," Microporous Materials, vol. 4, Issue 1 (1995), pp. 83-93.

Shu et al., "Methane Dehydroaromatization Over Mo/MCM-22 catalysts: A Highly Selective Catalyst for the Formation of Benzene," Catalysis Letters 70 (2000), pp. 67-73.

Xu et al., "A Novel Method for the Preparation of Zeolite ZSM-5," J. Chem. Soc., Chem. Commun. (1990), pp. 755-756.

A. Corma et al., "*Delaminated Zeolites: Combining the Benefits of Zeolites and Mesoporous Materials for Catalytic Uses*," Journal of Catalysis, vol. 186, pp. 57-63 (1999).

Baerlocher et al., "*Atlas of Zeolite Framework Types*," Elsevier Fifth Revised Edition, 2001.

Doraiswamy et al., "*Heterogeneous Reactions: Analysis, Examples, and Reactor Design, vol. 2: Fluid-Fluid-Solid Reactions*," John Wiley & Sons, New York, 1984.

Levenspiel, "*Chemical Reaction Engineering*," John Wiley & Sons, 1972.

Marques et al., "*Static crystallization of zeolites MCM-22 and MCM-49*," Microporous and Mesoporous Materials, 1999, vol. 32, pp. 131-145.

McCusker, "*Product Characterization by X-ray Powder Diffraction*," Verified Syntheses of Zeolite Materials, $2^{nd}$ Revised Edition, Robson ed, pp. 1-2, (Mar. 2002).

Stiles et al., "*Catalyst Manufacture*," Marcel Dekker, New York, 1995.

Szostak, "*Molecular Sieves—Principles of Synthesis and Identification*," $2^{nd}$ edition, Blackie Academic & Professional, London, 1998.

Thomas et al., "*Principles and Practice of Heterogeneous Catalysis*," VCH Publishers Inc., $1^{st}$ edition, 1997.

\* cited by examiner

XRD of As-synthesized Products of Comparative Example

XRD of As-synthesized Products of Example 1

SEM of Comparative Example

SEM of Example 1

PROCESS FOR MANUFACTURING MCM-22 FAMILY MOLECULAR SIEVES

CROSS REFERENCE TO RELATED APPLICATION

This application is a divisional of and claims priority to U.S. patent application Ser. No. 11/657,315, filed Jan. 24, 2007, now U.S. Pat. No. 7,799,316 which claims the benefit of U.S. Provisional Patent Application No. 60/773,135, filed Feb. 14, 2006, the disclosures of which are incorporated herein by reference in their entirety.

FIELD

This invention relates to a process of manufacturing MCM-22 family molecular sieves and the use of the same for hydrocarbon conversions.

BACKGROUND OF THIS INVENTION

Molecular sieve materials, both natural and synthetic, have been demonstrated in the past to have catalytic properties for various types of hydrocarbon conversion. Certain molecular sieves (e.g., zeolites, AlPOs, and/or mesoporous materials) are ordered, porous crystalline materials having a definite crystalline structure as determined by X-ray diffraction (XRD). Within the crystalline molecular sieve material there are a large number of cavities which may be interconnected by a number of channels or pores. These cavities and pores are uniform in size within a specific molecular sieve material. Since the dimensions of these pores are such as to accept for adsorption molecules of certain dimensions while rejecting those of larger dimensions, these materials have come to be known as "molecular sieve" and are utilized in a variety of industrial processes.

Such molecular sieves, both natural and synthetic, include a wide variety of positive ion-containing crystalline silicates. These silicates can be described as rigid three-dimensional framework of $SiO_4$ and Periodic Table (IUPAC 1997) Group IIIA element oxide (e.g., $AlO_4$). The tetrahedra are cross-linked by the sharing of oxygen atoms whereby the ratio of the total Group IIIA element (e.g., aluminum) and silicon atoms to oxygen atoms is 1:2. The electrovalence of the tetrahedra containing the Group IIIA element (e.g., aluminum) is balanced by the inclusion in the crystal of a cation, for example a proton, an alkali metal or an alkaline earth metal cation. This can be expressed wherein the ratio of the Group IIIA element (e.g., aluminum) to the number of various cations, such as $H^+$, $Ca^{2+}/2$, $Sr^{2+}/2$, $Na^+$, $K^+$, or $Li^+$, is equal to unity.

Molecular sieves that find application in catalysis include any of the naturally occurring or synthetic crystalline molecular sieves. Examples of these zeolites include large pore zeolites, intermediate pore size zeolites, and small pore zeolites. These zeolites and their isotypes are described in "Atlas of Zeolite Framework Types", eds. W. H. Meier, D. H. Olson and Ch. Baerlocher, Elsevier, Fifth Edition, 2001, which is hereby incorporated by reference. A large pore zeolite generally has a pore size of at least about 7 Å and includes LTL, VFI, MAZ, FAU, OFF, *BEA, and MOR framework type zeolites (IUPAC Commission of Zeolite Nomenclature). Examples of large pore zeolites include mazzite, offretite, zeolite L, VPI-5, zeolite Y, zeolite X, omega, and Beta. An intermediate pore size zeolite generally has a pore size from about 5 Å to less than about 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, MCM-22, silicalite 1, and silicalite 2. A small pore size zeolite has a pore size from about 3 Å to less than about 5.0 Å and includes, for example, CHA, ERI, KFI, LEV, SOD, and LTA framework type zeolites (IUPAC Commission of Zeolite Nomenclature). Examples of small pore zeolites include ZK-4, ZSM-2, SAPO-34, SAPO-35, ZK-14, SAPO-42, ZK-21, ZK-22, ZK-5, ZK-20, zeolite A, chabazite, zeolite T, gmelinite, ALPO-17, and clinoptilolite.

U.S. Pat. No. 4,439,409 refers to a crystalline molecular sieve composition of matter named PSH-3 and its synthesis from a hydrothermal reaction mixture containing hexamethyleneimine, an organic compound which acts as directing agent for synthesis of the MCM-56 (U.S. Pat. No. 5,362,697). Hexamethyleneimine is also taught for use in synthesis of crystalline molecular sieves MCM-22 (U.S. Pat. No. 4,954,325) and MCM-49 (U.S. Pat. No. 5,236,575). A molecular sieve composition of matter referred to as zeolite SSZ-25 (U.S. Pat. No. 4,826,667) is synthesized from a hydrothermal reaction mixture containing an adamantane quaternary ammonium ion. U.S. Pat. No. 6,077,498 refers to a crystalline molecular sieve composition of matter named ITQ-1 and its synthesis from a hydrothermal reaction mixture containing one or a plurality of organic additives.

The term "MCM-22 family material" (or "material of the MCM-22 family" or "molecular sieve of the MCM-22 family"), as used herein, includes one or more of:

(i) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

(ii) molecular sieves made from a common second degree building block, being a 2-dimensional tiling of such MWW framework topology unit cells, forming a monolayer of one unit cell thickness, preferably one c-unit cell thickness;

(iii) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize said molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1

(described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575) and MCM-56 (described in U.S. Pat. No. 5,362,697). The entire contents of said patents are incorporated herein by reference.

It is to be appreciated the MCM-22 family molecular sieves described above are distinguished from conventional large pore zeolite alkylation catalysts, such as mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, and ERB-1. Such molecular sieves are useful for alkylation of aromatic compounds. For example, U.S. Pat. No. 6,936,744 discloses a process for producing a monoalkylated aromatic compound, particularly cumene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of said molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstrom (Å).

The MCM-22 family molecular sieves including MCM-22, MCM-49, and MCM-56 have various applications in hydrocarbon conversion processes. However, they are expensive and time consuming for manufacturing. There is therefore a need for an improved high throughput process for manufacturing MCM-22 family molecular sieves, especially, the MCM-22 material. We have now found that the throughput of preparing the MCM-22 family molecular sieves is improved by improving formulation and crystallization conditions. The new improvements, together with shorter crystallization time, lower raw material usage, and/or higher yield, leads to lower production cost in manufacturing.

SUMMARY OF THIS INVENTION

In one embodiment, this invention relates to a method of manufacturing a molecular sieve of the MCM-22 family, said method comprising the steps of:
(a) providing a mixture comprising at least one source of ions of tetravalent element, at least one source of alkali metal hydroxide, at least one directing-agent (R), water, and optionally at least one source of ions of trivalent element, to form a mixture having the following mole composition:
$Y:X_2$=10 to infinity
$H_2O:Y$=1 to 20
$OH^-:Y$=0.001 to 2
$M^+:Y$=0.001 to 2
$R:Y$=0.001 to 0.34
wherein Y is a tetravalent element, X is a trivalent element, M is an alkali metal;
(b) treating said mixture to form said molecular sieve at crystallization conditions for less than 72 hr, wherein said crystallization conditions comprise a temperature in the range of from about 160° C. to about 250° C.; and
(c) recovering said molecular sieve.

In another embodiment, this invention relates to a method of crystallizing a molecular sieve of the MCM-22 family, said method comprising the steps of:
(a) providing a mixture comprising at least one source of ions of tetravalent element, at least one alkali metal hydroxide, at least one directing-agent (R), water, and optionally at least one source of ions of trivalent element, to form a mixture having the following mole composition:
$Y:X_2$=10 to infinity
$H_2O:Y$=1 to 20
$OH^-:Y$=0.001 to 2
$M^+:Y$=0.001 to 2
$R:Y$=0.001 to 0.34
wherein Y is a tetravalent element, X is a trivalent element, M is an alkali metal; and
(b) treating said mixture to form said molecular sieve at crystallization conditions for less than 72 hr, wherein said crystallization conditions comprise a temperature in the range of from about 160° C. to about 250° C. and a weight hourly throughput of at least 0.001 hr$^{-1}$.

In yet another embodiment, this invention relates to a molecular sieve of MCM-22 family manufactured by a method comprising the step of:
(a) providing a mixture comprising at least one tetravalent source, at least one alkali metal oxide, at least one directing-agent (R), water, and optionally one trivalent element source, to form a mixture having the following mole composition:
$Y:X_2$=10 to infinity
$H_2O:Y$=1 to 20
$OH^-:Y$=0.001 to 2
$M^+:Y$=0.001 to 2
$R:Y$=0.001 to 0.34
wherein Y is a tetravalent element, X is a trivalent element, M is an alkali metal; and
(b) treating said mixture to form said molecular sieve at crystallization conditions, wherein said crystallization conditions comprise a temperature in the range of from about 165° C. to about 250° C., and crystallization time less than 72 hr.

In an embodiment, this invention relates to a hydrocarbon conversion process, said process comprising the steps of:
(a) contacting a hydrocarbon feedstock with a molecular sieve of the MCM-22 family made by the method or process as recited in any preceding paragraphs or as specifically defined hereafter under conversion conditions to form a product; and
(b) withdrawing said product.

These and other facets of the present invention shall become apparent from the following detailed description, figure, and appended claims.

DETAILED DESCRIPTION OF THIS INVENTION

Introduction

Figure 1:
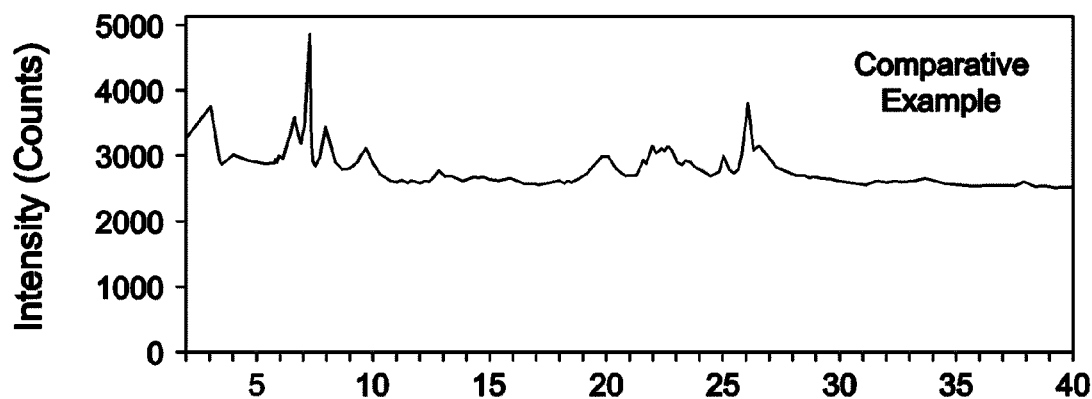
FIG. 1 is X-ray diffraction patterns of the crystalline material product of Comparative Example.

All patents, patent applications, test procedures, priority documents, articles, publications, manuals, and other documents cited herein are fully incorporated by reference to the extent such disclosure is not inconsistent with the present invention and for all jurisdictions in which such incorporation is permitted.

When numerical lower limits and numerical upper limits are listed herein, ranges from any lower limit to any upper limit are contemplated.

As used in this specification, the term "framework type" is used in the sense described in "Atlas of Zeolite Framework Types", eds. Ch. Baerlocher, W. H. Meier, and D. H. Olson, Elsevier, Fourth Edition, 2001.

The MCM-22, MCM-49, and MCM-56 crystalline materials may be distinguished from each other and other crystalline materials by the X-ray diffraction pattern.

The X-ray diffraction data described in this invention were collected with a Scintag diffraction system, equipped with a germanium solid state detector, using copper K-alpha radiation. The diffraction data were recorded by step-scanning at 0.02 degrees of two-theta (2θ), where theta (θ) is the Bragg angle, and a counting time of 10 seconds for each step. The interplanar spacings, d's, were calculated in Å units, and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols VS=very strong (greater than 60 to 100), S=strong (greater than 40 to 60), M=medium (greater than 20 to 40) and W=weak (0-20). It should be understood that diffraction data listed as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history. Other changes in diffraction patterns can be indicative of important differences between materials, which is the case for comparing MCM-22 with similar materials, e.g., MCM-49, MCM-56, and PSH-3.

It should be understood that this X-ray diffraction pattern is characteristic of all the species of the present crystalline composition. The sodium form as well as other cationic forms reveal substantially the same pattern with some minor shifts in interplanar spacing and variation in relative intensity. Other minor variations can occur, depending on the Y to X, e.g., silicon to aluminum, ratio of the particular sample, as well as its degree of thermal (e.g., calcination).

Known MCM-22

The known MCM-22 crystalline material has a composition involving the molar relationship:

$X_2O_3:(n)YO_2$, wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, the material has a formula, on an anhydrous basis and in terms of moles of oxides per n moles of $YO_2$, as follows:

$(0.005-0.1)M_2O:(1-4)R:X_2O_3:nYO_2$ wherein M is an alkali or alkaline earth metal, and R is an organic moiety. The M and R components are associated with the material as a result of their presence during synthesis, and are easily removed by post-synthesis methods hereinafter more particularly described.

In its calcined form, the known MCM-22 crystalline material has an X-ray diffraction pattern which is distinguished from the patterns of other known crystalline materials by the lines listed in Table I below:

TABLE I

| Interplanar d-Spacing (Å) | Relative Intensity, $I/I_o$ × 100 |
|---|---|
| 30.0 ± 2.2 | W-M |
| 22.1 ± 1.3 | W | more specifically by the lines listed in Table II below:

TABLE II

| Interplanar d-Spacing (Å) | Relative Intensity, $I/I_o$ × 100 |
|---|---|
| 30.0 ± 2.2 | W-M |
| 22.1 ± 1.3 | W |
| 3.91 ± 0.07 | M-VS | and yet more specifically by the lines listed in Table III below:

TABLE III

| Interplanar d-Spacing (Å) | Relative Intensity, $I/I_o$ × 100 |
|---|---|
| 30.0 ± 2.2 | W-M |
| 22.1 ± 1.3 | W |
| 6.00 ± 0.10 | M-W |
| 4.64 ± 0.08 | W |
| 4.06 ± 0.07 | W-S |
| 3.91 ± 0.07 | M-VS |

Figure 2:
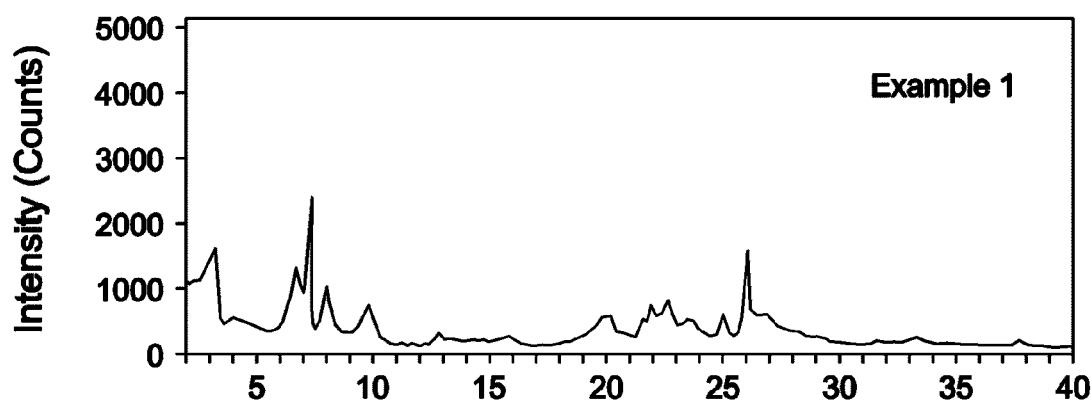
FIG. 2 is X-ray diffraction patterns of the crystalline material product of Example 1.
Figure 3:
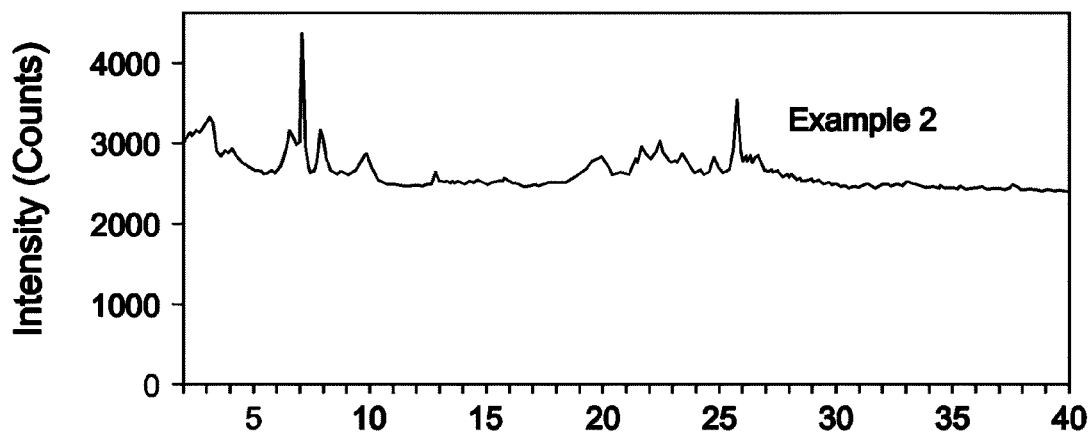
FIG. 3 is X-ray diffraction patterns of the crystalline material product of Example 2.
Figure 4:
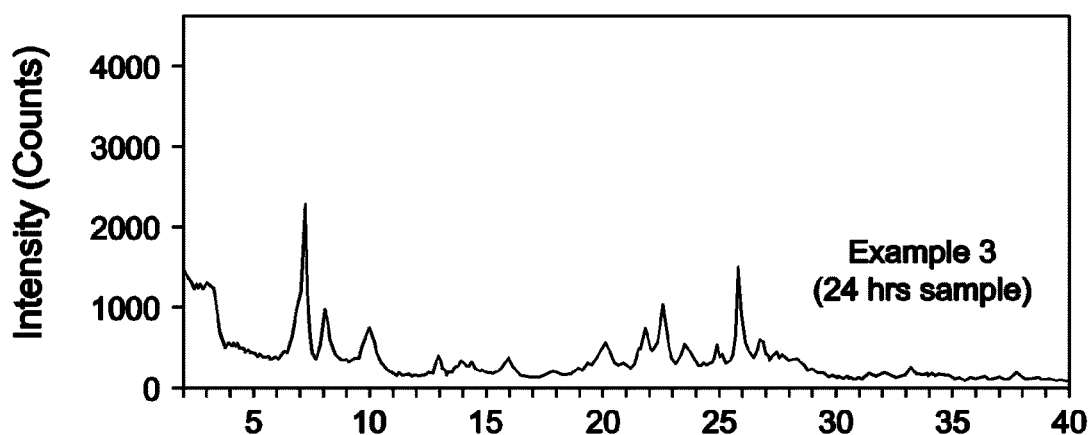
FIG. 4 is X-ray diffraction patterns of the crystalline material products of Example 3 at 24 hours.

The MCM-22 family molecular sieve composition of this invention is characterized by at least one additional peak between 26.6 to 29° (2θ) in its X-ray diffraction pattern of as-synthesized material, which is exemplified by reference example and example 1 (FIGS. 1 and 2).

Figure 5:
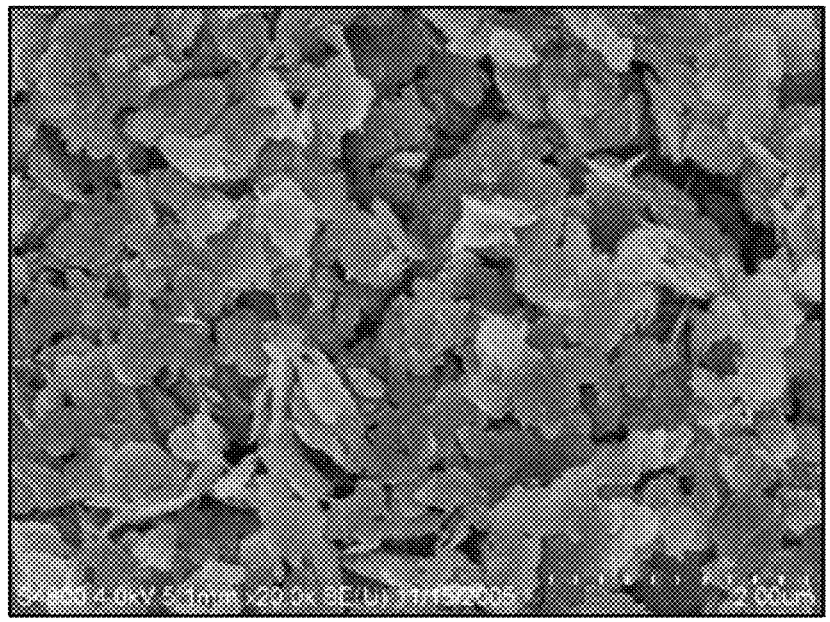
FIG. 5 is the SEM image of the crystalline material product of Comparative Example.
Figure 6:
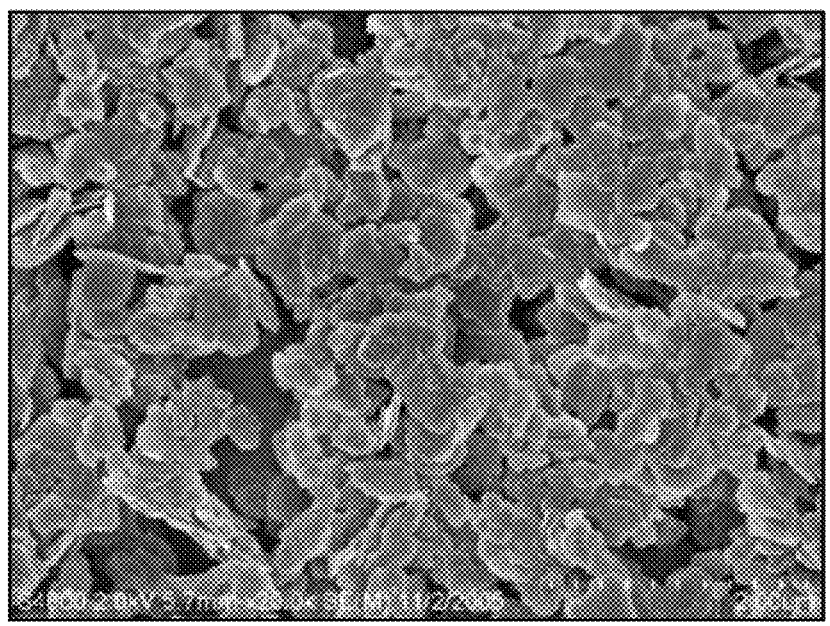
FIG. 6 is the SEM image of the crystalline material product of Example 1.

The SEM image of the MCM-22 molecular sieve produced according to the method of manufacturing of U.S. Pat. No. 4,954,325 is shown in FIG. 5. The MCM-22 molecular sieve according to method of manufacturing of U.S. Pat. No. 4,954,325 has a thin layered less defined hexagonal platelets morphology and an average platelet diameter of less than about 1 μm. The SEM image of the MCM-22 family molecular sieve of this invention is shown in FIG. 6. The MCM-22 family molecular sieve of this invention (FIG. 6) has a thin layered better defined hexagonal platelets morphology than these in FIG. 5 and substantially similar average platelet diameter. However, the particles of the MCM-22 of this invention are generally thicker than the particles of the MCM-22 produced according to the method of manufacturing of U.S. Pat. No. 4,954,325.

Known MCM-49

The known MCM-49 crystalline material has a composition involving the molar relationship:

$$X_2O_3:(n)YO_2,$$

wherein X is a trivalent element, such as aluminum, boron, iron and/or gallium, preferably aluminum; Y is a tetravalent element such as silicon and/or germanium, preferably silicon; and n is less than about 35, e.g., from 2 to less than about 35, usually from about 10 to less than about 35, more usually from about 15 to about 31. In the as-synthesized form, the material has a formula, on an anhydrous basis and in terms of moles of oxides per n moles of $YO_2$, as follows:

$$(0.1-0.6)M_2O:(1-4)R:X_2O_3:nYO_2$$

wherein M is an alkali or alkaline earth metal, and R is an organic moiety. The M and R components are associated with the material as a result of their presence during crystallization, and are easily removed by post-crystallization methods hereinafter more particularly described.

In the as-synthesized form, the known MCM-49 crystalline material has an X-ray diffraction pattern which is distinguished from the patterns of other known as-synthesized or thermally treated crystalline materials by the lines listed in Table IV below:

TABLE IV

| Interplanar d-Spacing (Å) | Relative Intensity, $I/I_o \times 100$ |
| --- | --- |
| 13.15 ± 0.26 | W-S* |
| 12.49 ± 0.24 | VS |
| 11.19 ± 0.22 | M-S |
| 6.43 ± 0.12 | W |
| 4.98 ± 0.10 | W |
| 4.69 ± 0.09 | W |
| 3.44 ± 0.07 | VS |
| 3.24 ± 0.06 | W |

*shoulder

The X-ray diffraction peak at 13.15±0.26 Å Units (Å) is usually not fully resolved for known MCM-49 from the intense peak at 12.49±0.24 Å, and is observed as a shoulder of this intense peak. For this reason, the precise intensity and position of the 13.15±0.26 Å peak are difficult to determine within the stated range.

In its calcined form, the known MCM-49 crystalline material of this invention transforms to a single crystal phase with little or no detectable impurity crystal phases having an X-ray diffraction pattern which is not readily distinguished from that of known MCM-22, but distinguishable from the patterns of other known crystalline materials. The X-ray diffraction pattern of the calcined form of known MCM-49 includes the lines listed in Table V below:

TABLE V

| Interplanar d-Spacing (Å) | Relative Intensity, $I/I_o \times 100$ |
| --- | --- |
| 12.41 ± 0.24 | VS |
| 11.10 ± 0.22 | S |
| 8.89 ± 0.17 | M-S |
| 6.89 ± 0.13 | W |
| 6.19 ± 0.12 | M |
| 6.01 ± 0.12 | W |
| 5.56 ± 0.11 | W |
| 4.96 ± 0.10 | W |
| 4.67 ± 0.09 | W |
| 4.59 ± 0.09 | W |
| 4.39 ± 0.09 | W |
| 4.12 ± 0.08 | W |
| 4.07 ± 0.08 | W-M |
| 3.92 ± 0.08 | W-M |
| 3.75 ± 0.07 | W-M |
| 3.57 ± 0.07 | W |
| 3.43 ± 0.07 | S-VS |
| 3.31 ± 0.06 | W |
| 3.21 ± 0.06 | W |
| 3.12 ± 0.06 | W |
| 3.07 ± 0.06 | W |
| 2.83 ± 0.05 | W |
| 2.78 ± 0.05 | W |
| 2.69 ± 0.05 | W |
| 2.47 ± 0.05 | W |
| 2.42 ± 0.05 | W |
| 2.38 ± 0.05 | W |

Formulation of the Hydrothermal Reaction Mixtures

Synthetic zeolites are often prepared from aqueous hydrothermal reaction mixtures (or synthesis mixture(s)/synthesis gel(s)) comprising sources of appropriate oxides. Organic directing agents may also be included in the hydrothermal reaction mixture for the purpose of influencing the production of a zeolite having the desired structure. The use of such directing agents is discussed in an article by Lok et al. entitled "The Role of Organic Molecules in Molecular Sieve Synthesis" appearing in Zeolites, Vol. 3, October, 1983, pp. 282-291.

After the components of the hydrothermal reaction mixture are properly mixed with one another, the hydrothermal reaction mixture is subjected to appropriate crystallization conditions. Such conditions usually involve heating of the hydrothermal reaction mixture to an elevated temperature possibly with stirring. Room temperature aging of the hydrothermal reaction mixture is also desirable in some instances.

After the crystallization of the hydrothermal reaction mixture is complete, the crystalline product may be recovered from the remainder of the hydrothermal reaction mixture, especially the liquid contents thereof. Such recovery may involve filtering the crystals and washing these crystals with water. However, in order to remove the entire undesired residue of the hydrothermal reaction mixture from the crystals, it is often necessary to subject the crystals to a high temperature calcination e.g., at 500° C., possibly in the presence of oxygen. Such a calcination treatment not only removes water from the crystals, but this treatment also serves to decompose and/or oxidize the residue of the organic directing agent which may be occluded in the pores of the crystals, possibly occupying ion exchange sites therein.

This MCM-22 material may be prepared from a hydrothermal reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, said hydrothermal reaction mixture having a composition, in terms of mole ratios of oxides, within the following ranges:

TABLE VI

| Reactants | Useful | Preferred |
| --- | --- | --- |
| $YO_2/X_2O_3$ | 10 to infinity | 15-50 |
| $H_2O/YO_2$ | 1-20 | 5-15 |
| $OH^-/YO_2$ | 0.01-0.5 | 0.1-0.3 |
| $M/YO_2$ | 0.01-0.5 | 0.1-0.3 |
| $R/YO_2$ | 0.001-0.5 | 0.1-0.34 |

This known MCM-49 material can be prepared from a hydrothermal reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, said hydrothermal reaction mixture having a composition, in terms of mole ratios of oxides, within the following ranges:

TABLE VII

| Reactants | Useful | Preferred |
|---|---|---|
| $YO_2/X_2O_3$ | 12-less than 35 | 15-30 |
| $H_2O/YO_2$ | 1-20 | 5-15 |
| $OH^-/YO_2$ | 0.01-0.5 | 0.1-0.3 |
| $M/YO_2$ | 0.01-0.5 | 0.1-0.3 |
| $R/YO_2$ | 0.001-0.5 | 0.1-0.34 |

The sources of the various elements required in the final product may be any of those in commercial use or described in the literature, as may the method of preparation of the synthesis mixture.

It will be understood by a person skilled in the art that the synthesis mixture having a composition within the molar ranges as discussed above means that the synthesis mixture is the product of mixing, adding, reacting, or by any means of providing such a mixture, wherein such product has a composition within the molar ranges as discussed above. The product of mixing, adding, reacting, or by any means of providing such a mixture may or may not containing individual ingredients when the synthesis mixture was prepared. The product of mixing, adding, reacting, or by any means of providing such a mixture, may even containing reaction product of individual ingredients when the synthesis mixture was prepared by mixing, adding, reacting, or by any means of providing such a mixture.

The source of ions of trivalent element $X_2O_3$, e.g., aluminum, boron, gallium, and iron, is preferably aluminum sulphate or hydrated alumina. Other aluminum sources include, for example, other water-soluble aluminum salts, sodium aluminate, or an alkoxide, e.g., aluminum isopropoxide, or aluminum metal, e.g., in the form of chips.

The alkali metal is advantageously potassium or sodium, the sodium source advantageously being sodium hydroxide or sodium aluminate.

Directing agent R is selected from the group consisting of cycloalkylamine, azacycloalkane, diazacycloalkane, and mixtures thereof, alkyl comprising from 5 to 8 carbon atoms. Non-limiting examples of R include cyclopentylamine, cyclohexylamine, cycloheptylamine, hexamethyleneimine, heptamethyleneimine, homopiperazine, and combinations thereof.

A factor affecting the cost and the product quality of the synthesis of a molecular sieve is the amount of the directing agent. The directing agent is generally the most expensive reactant(s) in the hydrothermal reaction mixture of many crystalline molecular sieves. The lower the amount of the directing agent in the hydrothermal reaction mixture, the cheaper the final molecular sieve produced. The term "low directing agent" as used herein means the molar ratio of the directing agent over the tetravalent element in the hydrothermal reaction mixture is less than 0.5, preferably less than 0.34, even more preferably less than 0.2, and most preferably less than 0.15.

In one embodiment, this invention R:Y molar ratio ranges from 0.001 to 0.5, preferably from 0.001 to 0.34, more preferably from 0.001 to 0.3, even more preferably from 0.001 to 0.2, and most preferably from 0.1 to 0.15.

One factor affecting the synthesis of a molecular sieve is the solid-content in a hydrothermal reaction mixture. The term "solid-content" used herein means the weight percentage of both trivalent and tetravalent oxides in the hydrothermal reaction mixture. It can be measured by dividing the weight of both trivalent and tetravalent oxides in the hydrothermal reaction mixture by the total weight of the hydrothermal reaction mixture as following:

$$\text{solid-content}(\%) = \frac{\text{weight of the oxides in the hydrothermal reaction mixture}}{\text{total weight of the hydrothermal reaction mixture}} \times 100\%$$

The term "high solid" used herein means that the solid-content of a hydrothermal reaction mixture is at least 12 wt. %, preferably at least 15 wt. %, more preferably at least 18 wt. %, even more preferably at least 20 wt. %, and most preferably at least 30 wt. %.

It should be realized that the hydrothermal reaction mixture components can be supplied by more than one source. The hydrothermal reaction mixture can be prepared either batchwise or continuously. Crystal size and crystallization time of the new crystalline material will vary with the nature of the hydrothermal reaction mixture employed and the crystallization conditions.

It will be understood by a person skilled in the art that the MCM-22 family material may contain impurities, such as amorphous materials; unit cells having non-MWW framework topologies (e.g., MFI, MTW); and/or other impurities (e.g., heavy metals and/or organic hydrocarbons). The MCM-22 family materials of this invention have preferably substantially free of non-MCM-22 family material(s). The term "substantially free of non-MCM-22 family material(s)" used herein means the MCM-22 family material of this invention preferably contains the minor proportion (less than 50 wt. %), preferably less than 20 wt. %, more preferably less than 10 wt. %, even more preferably less than 5 wt. %, and most preferably less than 1 wt. %, of such impurities in the MCM-22 family materials, which weight percent (wt. %) values are based on the combined weight of impurities and pure phase MCM-22 family materials.

Crystallization Conditions

Crystallization of the present crystalline material can be carried out at either static or stirred condition in a reactor vessel, such as for example, autoclaves. The total useful range of temperatures for crystallization is from about 160° C. to about 250° C. for a time sufficient for crystallization to occur at the temperature used, e.g., from about 3 hours to about 72 hours, preferably from about 10 hours to about 48 hours, and most preferably from about 10 hours to about 24 hours. Thereafter, the crystals are separated from the liquid and recovered. The procedure may include an aging period, either at room temperature or, preferably, at a moderately elevated temperature, before the hydrothermal treatment ("hydrothermal reaction") at more elevated temperature. The latter may include a period of gradual or stepwise variation in temperature.

For most of the applications, the hydrothermal reaction is carried out with any type of agitation, e.g., stirring or rotating the vessel around a horizontal axis (tumbling).

One factor affecting the synthesis of a molecular sieve, for example, cycle time and product quality, is the hydrothermal reaction temperature. High temperature, e.g., greater than 200° C., may damage the directing agent in the hydrothermal reaction mixture. Generally, the higher the temperature, the faster the crystallization rate. However, higher temperature may damage the expensive directing agent, which may impact the product quality, e.g., final product containing impurities. The term "high temperature" as used herein means the crystallization temperature in the range of from about 160 to about 250° C. for the synthesis of a molecular sieve of MCM-22 family materials.

The term "throughput" used herein means the amount of crystalline molecular sieve produced per unit time (hour) and per unit volume of the hydrothermal reaction mixture (volume hourly throughput) or per unit weight of the hydrothermal reaction mixture (weight hourly throughput). The higher the throughput, the more crystalline molecular sieve produced per unit volume of the reactor and per unit amount of time. Therefore, for the same amount of the crystalline molecular sieve synthesized, the higher the throughput, generally the smaller the reactor (autoclave) needed or the shorter the time required for each synthesis. The volume hourly throughput for a synthesis may be calculated by dividing the weight of the molecular sieve produced in the dried cake (the solid product after crystallization dried at about 120° C.) with the volume of the reaction mixture and the total time required for the crystallization (hereinafter "cycle time required for the crystallization"). The cycle time required for the crystallization is the time required for the completion of the reaction ("crystallization") under the crystallization conditions, which does not include the time for charging and/or aging the hydrothermal reaction mixture, filtering, washing, and drying the product. The volume hourly throughput for a synthesis is calculated as following:

$$\text{volume hourly throughput} = \frac{\text{volume of the molecular sieve produced (dried at about 120° C.)}}{\left(\begin{array}{c}\text{volume of the hydrothermal}\\ \text{reaction mixture}\end{array}\right) \times (\text{cycle time})}$$

The weight hourly throughput for a synthesis may be calculated by dividing the weight of the molecular sieve produced in the dried cake (the solid product after crystallization dried at about 120° C.) with the weight of the hydrothermal reaction mixture and the cycle time required for the crystallization as following:

$$\text{weight hourly throughput} = \frac{\text{weight of the molecular sieve produced (dried at about 120° C.)}}{\left(\begin{array}{c}\text{weight of the hydrothermal}\\ \text{reaction mixture}\end{array}\right) \times (\text{cycle time})}$$

In one aspect of this invention, the weight hourly throughput for this invention is at least 0.001 $hr^{-1}$, preferably at least 0.002 $hr^{-1}$, more preferably at least 0.004 $hr^{-1}$, and most preferably at least 0.008 $hr^{-1}$.

The weight hourly throughput of a synthesis may be adjusted by changing solid-content, amount of seed used in the synthesis gel, crystallization temperature, time for crystallization, and/or any combination thereof. The weight hourly throughput and these parameters mentioned above are interrelated. Changing one parameter may affect other parameters. For example, by increasing weight hourly throughput of a synthesis under certain crystallization conditions, e.g., crystallization temperature and time, the solid-content and/or the amount of seed crystal may have to increase.

In one embodiment of this invention, the process of manufacturing a molecular sieve of MCM-22 family materials further comprises a step to recovering the directing agent by flashing and condensing the directing agent (not incorporated in the molecular sieve product) and water in the hydrothermal reaction mixture after crystallization. The recovered directing agent aqueous solution may be reused as the directing agent in another synthesis. The flashing/condensing may be conveniently performed by opening a valve on the autoclave used for the synthesis, condensing and collecting vapor released from the autoclave in a liquid phase. The condensed vapor contains at least a portion of the templating agent(s) in the autoclave which may be reused for synthesis. In one embodiment of this invention, at least 50 wt. %, preferably at least 80 wt. % of the directing agent not incorporated in the molecular sieve product, may be recovered by the flashing and condensing step of this invention.

Optionally the hydrothermal reaction mixture may contain seed crystals. It is well known that seeding a molecular sieve synthesis mixture frequently has beneficial effects, for example in controlling the particle size of the product, avoiding the need for an organic template, accelerating synthesis, and improving the proportion of product that is of the intended framework type. In one embodiment of this invention, synthesis of the crystalline molecular sieve is facilitated by the presence of at least 0.0001 wt. %, preferably 0.001 wt. %, more preferably 0.01 wt. %, even more preferably 0.1 wt. %, optionally 5 wt. % to about 20 wt. %, seed crystals based on total weight of the hydrothermal reaction mixture.

In one embodiment, the crystalline molecular sieve of this invention comprises at least one of MCM-22, MCM-49, MCM-56, and a mix-phase of MCM-22, MCM-49, and MCM-56.

We discovered an improved formulation for manufacturing a molecular sieve of MCM-22 family materials (e.g., MCM-22, MCM-49, and/or MCM-56) by the combination of high solid content, low directing agent usage, and optionally seeding at improved crystallization conditions including high temperature, stirring, and optionally recovering, recycling, and reusing the directing agent. By recovering, recycling, and reusing the directing agent, the hydrothermal reaction mixture of this invention uses much less of the costly and toxic directing agent (e.g., HMI).

A summary of the molecular sieves and/or zeolites, in terms of production, modification and characterization of molecular sieves, is described in the book "Molecular Sieves—Principles of Synthesis and Identification"; (R. Szostak, Blackie Academic & Professional, London, 1998, Second Edition). In addition to molecular sieves, amorphous materials, chiefly silica, aluminum silicate and aluminum oxide, have been used as adsorbents and catalyst supports. A number of long-known techniques, like spray drying, prilling, pelletizing and extrusion, have been and are being used to produce macrostructures in the form of, for example, spherical particles, extrudates, pellets and tablets of both micropores and other types of porous materials for use in catalysis, adsorption and ion exchange. A summary of these techniques is described in "Catalyst Manufacture," A. B. Stiles and T. A. Koch, Marcel Dekker, New York, 1995.

Catalysis and Adsorption

To the extent desired, however, the original metal cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB and VIII of the Periodic Table of the Elements (IUPAC 2001).

The MCM-22 family molecular sieve of this invention, when employed either as an adsorbent or as a catalyst in an organic compound conversion process is ideally dehydrated, at least partially. This can be done by heating to a temperature in the range of 200° C. to 595° C. in an atmosphere such as air, nitrogen, etc. and at atmospheric, subatmospheric or superatomspheric pressures for between 30 minutes and 48 hours. Dehydration can also be performed at room temperature merely by placing the silicate in a vacuum, but a longer time is required to obtain a sufficient amount of dehydration.

When used as a catalyst, the MCM-22 family molecular sieve of this invention is preferably subjected to thermal treatment to remove part or all of any organic constituent. The MCM-22 family molecular sieve can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be in the composition by way of cocrystallization, exchanged into the composition to the extent a Group IIIA element, e.g., aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The above MCM-22 family molecular sieve, especially in its metal, hydrogen and ammonium forms can be beneficially converted to another form by thermal treatment. This thermal treatment is generally performed by heating one of these forms at a temperature of at least 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermal treated product is particularly useful in the catalysis of certain hydrocarbon conversion reactions. The thermally treated product, especially in its metal, hydrogen and ammonium forms, is particularly useful in the catalysis of certain organic, e.g., hydrocarbon, conversion reactions. Non-limiting examples of such reactions include those described in U.S. Pat. Nos. 4,954,325; 4,973,784; 4,992,611; 4,956,514; 4,962,250; 4,982,033; 4,962,257; 4,962,256; 4,992,606; 4,954,663; 4,992,615; 4,983,276; 4,982,040; 4,962,239; 4,968,402; 5,000,839; 5,001,296; 4,986,894; 5,001,295; 5,001,283; 5,012,033; 5,019,670; 5,019,665; 5,019,664; and 5,013,422, each incorporated herein by reference as to the description of said catalytic reactions.

The crystals prepared by the instant invention can be shaped into a wide variety of particle sizes. Generally speaking, the particles can be in the form of a powder, a granule, or a molded product, such as an extrudate. In cases where the catalyst is molded, such as by extrusion, the crystals can be extruded before drying or partially dried and then extruded.

The MCM-22 family molecular sieve of this invention may be used as an adsorbent, such as for separating at least one component from a mixture of components in the vapor or liquid phase having differential sorption characteristics with respect to the MCM-22 family molecular sieve of this invention. Therefore, at least one component can be partially or substantially totally separated from a mixture of components having differential sorption characteristics with respect to the MCM-22 family molecular sieve of this invention by contacting the mixture with the MCM-22 family molecular sieve of this invention to selectively sorb the one component.

The MCM-22 family molecular sieves of this invention are useful as catalyst in a wide range of processes, including separation processes and hydrocarbon conversion processes. Specific examples of hydrocarbon conversion processes which are effectively catalyzed by the MCM-22 family molecular sieve of this invention, by itself or in combination with one or more other catalytically active substances including other crystalline catalysts, include the following:

(i) alkylation of aromatic hydrocarbons, e.g., benzene, with long chain olefins, e.g., $C_{14}$ olefin, with reaction conditions including a temperature of from about 340° C. to about 500° C., a pressure of from about 101 to about 20200 kPa-a, a weight hourly space velocity of from about 2 $hr^{-1}$ to about 2000 $hr^{-1}$ and an aromatic hydrocarbon/olefin mole ratio of from about 1/1 to about 20/1, to provide long chain alkyl aromatics which can be subsequently sulfonated to provide synthetic detergents;

(ii) alkylation of aromatic hydrocarbons with gaseous olefins to provide short chain alkyl aromatic compounds, e.g., the alkylation of benzene with propylene to provide cumene, with reaction conditions including a temperature of from about 10° C. to about 125° C., a pressure of from about 101 to about 3030 kPa-a, and an aromatic hydrocarbon weight hourly space velocity (WHSV) of from 5 $hr^{-1}$ to about 50 $hr^{-1}$;

(iii) alkylation of reformate containing substantial quantities of benzene and toluene with fuel gas containing $C_5$ olefins to provide, inter alia, mono- and dialkylates with reaction conditions including a temperature of from about 315° C. to about 455° C., a pressure of from about 3000 to about 6000 kPa-a, a WHSV-olefin of from about 0.4 $hr^{-1}$ to about 0.8 $hr^{-1}$, a WHSV-reformate of from about 1 $hr^{-1}$ to about 2 $hr^{-1}$ and a gas recycle of from about 1.5 to 2.5 vol/vol fuel gas feed;

(iv) alkylation of aromatic hydrocarbons, e.g., benzene, toluene, xylene and naphthalene, with long chain olefins, e.g., $C_{14}$ olefin, to provide alkylated aromatic lube base stocks with reaction conditions including a temperature of from about 160° C. to about 260° C. and a pressure of from about 2600 to 3500 kPa-a;

(v) alkylation of phenols with olefins or equivalent alcohols to provide long chain alkyl phenols with reaction conditions including a temperature of from about 200° C. to about 250° C., a pressure of from about 1500 to 2300 kPa-a and a total WHSV of from about 2 $hr^{-1}$ to about 10 $hr^{-1}$;

(vi) conversion of light paraffins to olefins and aromatics with reaction conditions including a temperature of from about 425° C. to about 760° C. and a pressure of from about 170 to about 15000 kPa-a;

(vii) conversion of light olefins to gasoline, distillate and lube range hydrocarbons with reaction conditions including a temperature of from about 175° C. to about 375° C. and a pressure of from about 800 to about 15000 kPa-a;

(viii) two-stage hydrocracking for upgrading hydrocarbon streams having initial boiling points above about 260° C. to premium distillate and gasoline boiling range products in a first stage using the MCM-22 family molecular sieve of this invention in combination with a Group VIII metal as catalyst with effluent therefrom being reaction in a second stage using zeolite Beta, also in combination with a Group VIII metal, as catalyst, the reaction conditions including a temperature of from about 340° C. to about 455° C., a pressure of from about 3000 to about 18000 kPa-a, a hydrogen circulation of from about 176 to about 1760 liter/liter and a liquid hourly space velocity (LHSV) of from about 0.1 to 10 hr$^{-1}$;

(ix) a combination hydrocracking/dewaxing process in the presence of the MCM-22 family molecular sieve of this invention and a hydrogenation component as catalyst, or a mixture of such catalyst and zeolite Beta, with reaction conditions including a temperature of from about 350° C. to about 400° C., a pressure of from about 10000 to about 11000 kPa-a, an LHSV of from about 0.4 to about 0.6 hr$^{-1}$ and a hydrogen circulation of from about 528 to about 880 liter/liter;

(x) reaction of alcohols with olefins to provide mixed ethers, e.g., the reaction of methanol with isobutene and/or isopentene to provide methyl-t-butyl ether (MTBE) and/or t-amyl methyl ether (TAM) with conversion conditions including a temperature of from about 20° C. to about 200° C., a pressure of from 200 to about 20000 kPa-a, a WHSV (gram-olefin per hour gram-zeolite) of from about 0.1 hr$^{-1}$ to about 200 hr$^{-1}$ and an alcohol to olefin molar feed ratio of from about 0.1/1 to about 5/1;

(xi) toluene disproportionations with $C_9$+ aromatics as co-feed with reaction conditions including a temperature of from about 315° C. to about 595° C., a pressure of from about 101 to about 7200 kPa-a, a hydrogen/hydrocarbon mole ratio of from about 0 (no added hydrogen) to about 10 and a WHSV of from about 0.1 hr$^{-1}$ to about 30 hr$^{-1}$;

(xii) preparation of the pharmaceutically-active compound 2-(4-isobutylphenyl) propionic acid, i.e. ibuprofen, by reacting isobutylbenzene with propylene oxide to provide the intermediate 2-(4-isobutylphenyl) propanol followed by oxidation of the alcohol to the corresponding carboxylic acid;

(xiii) use as an acid-binding agent in the reaction of amines with heterocyclic fiber-reactive components in preparation of dyes to prepare practically salt-free reactive dye-containing solution, as in German Patent No. DE 3,625,693, incorporated entirely herein by reference;

(xiv) as the absorbent for separating 2,6-toluene diisocyanate (2,6-TDI) from isomers if TDI as in U.S. Pat. No. 4,721,807, incorporated entirely herein by reference, whereby a feed mixture comprising 2,6-TDI and 2,4-TDI is contacted with the present MCM-22 family molecular sieve which has been cation-exchanged with K ions to absorb the 2,6-TDI, followed by recovering the 2,6-TDI by desorption with desorbent material comprising toluene;

(xv) as the absorbent for separating 2,4-TDI from its isomers as in U.S. Pat. No. 4,721,806, incorporated entirely herein by reference, whereby a feed mixture comprising 2,4-TDI and 2,6-TDI is contact with the present MCM-22 family molecular sieve which has been cation-exchanged with Na, Ca Li and/or Mg ions to absorb the 2,4-TDI, followed by recovering the 2,4-TDI by desorption with desorbent material comprising toluene; and (xvi) in a process for decreasing the durene content of a 90-200° C.+ bottoms fraction obtained from the catalytic conversion of methanol to gasoline which comprises contacting said durene-containing bottoms fraction with hydrogen over a catalyst of the present MCM-22 family molecular sieve with a hydrogenation metal, at conditions including a temperature of from about 230° C. to about 425° C. and a pressure of from about 457 to about 22000 kPa-a.

In an embodiment, the MCM-22 family molecular sieves of this invention may be used in processes that co-produce phenol and ketones that proceed through benzene alkylation, followed by formation of the alkylbenzene hydroperoxide and cleavage of the alkylbenzene hydroperoxide into phenol and ketone. In such processes, the MCM-22 family molecular sieves of this invention are used in the first step, that is, benzene alkylation. Examples of such processes includes processes in which benzene and propylene are converted to phenol and acetone, benzene and C4 olefins are converted to phenol and methyl ethyl ketone, such as those described for example in international application PCT/EP2005/008557, benzene, propylene and C4 olefins are converted to phenol, acetone and methyl ethyl ketone, which, in this case can be followed by conversion of phenol and acetone to bis-phenol-A as described in international application PCT/EP2005/008554, benzene is converted to phenol and cyclohexanone, or benzene and ethylene are converted to phenol and methyl ethyl ketone, as described for example in PCT/EP2005/008551.

The MCM-22 family molecular sieves of this invention are useful in benzene alkylation reactions where selectivity to the monoalkylbenzene is required. Furthermore, the MCM-22 family molecular sieves of this invention is particularly useful to produce selectively sec-butylbenzene from benzene and C4 olefin feeds that are rich in linear butenes, as described in international application PCT/EP2005/008557. Preferably, this conversion is carried out by co-feeding benzene and the C4 olefin feed with the catalyst of the present invention, at a temperature of about 60° C. to about 260° C., for example of about 100° C. to 200° C., a pressure of 7000 kPa-a or less, and a feed weight hourly space velocity (WHSV) based on C4 alkylating agent of from about 0.1 to 50 hr$^{-1}$ and a molar ratio of benzene to C4 alkylating agent from about 1 to about 50.

The MCM-22 family molecular sieves of this invention are also useful catalyst for transalkylations, such as, for example, polyalkylbenzene transalkylations.

In the case of many catalysts, it is desired to incorporate the new crystal with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the new crystal, i.e. combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e. clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dictite, narcite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the new crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided MCM-22 family molecular sieve and inorganic oxide matrix vary widely, with the crystal content ranging from about 1 to about 90 percent by weight and more usually, particularly when the composite is prepared in the form of beads, in the range of about 2 to about 80 wt. % of the composite.

EXAMPLES

The following examples illustrate exemplary preferred embodiments:

In these examples, the XRD diffraction patterns of the as-synthesized materials were recorded on an X-Ray Powder Diffractometer using copper Kα radiation in the 2θ range of 2 to 40 degrees.

The SEM images were obtained on a HITACHI S4800 Field Emission Scanning Electron Microscope (SEM).

The yields were estimated based on an assumption that all aluminum and about 85 wt. % of silicon were incorporated in the molecular sieve product. The molecular sieve product contained about 15 wt. % of water and templating agent.

The crystallinity is defined as the sum of the two main peaks, 7.1 and 26 (2θ), to the ratio of the sum of the same peaks in the standard (reference example), multiplied by 100.

Comparative Example

A hydrothermal reaction mixture was prepared from water, Hexamethyleneimine (HMI) (Sigma-Aldrich Company), silica (Ultrasil™, Degussa Corp.), 45 wt. % sodium aluminate solution, and 50 wt. % sodium hydroxide solution. The mixture had the following molar composition:

|  | Reference Example |
|---|---|
| Molar composition | |
| $SiO_2/Al_2O_3$ | ~30 |
| $H_2O/SiO_2$ | ~19.8 |
| $OH^-/SiO_2$ | ~0.17 |
| $Na^+/SiO_2$ | ~0.17 |
| $HMI/SiO_2$ | ~0.35 |
| Solid-content (wt. %) | |
| Crystallization conditions | |
| Temperature (° C.) | 150 |
| Stirring speed (RPM) | 250 |
| Time (hr) | 72 |
| Estimated Yield (wt. %) | ~11.7 |
| XRD Result | Pure Phase MCM-22 |
| Crystallinity (%) | 100 |
| $SiO_2/Al_2O_3$ (molar ratio) | ~23 |
| Total Surface Area (m²/g) | 653 |
| Micropore Surface Area (m²/g) | 530 |
| External Surface Area (m²/g) | 123 |
| Weight Hourly Throughput (hr⁻¹) | 0.0019 |
| Mesitylene uptake (mg/g) | 29.8 |
| Mesitylene sorption rate (mg/g/min) | 68 |

The mixture was crystallized at 150° C. in an autoclave with stirring at 250 rotation per minute (RPM) for 72 hours. After crystallization, the hydrothermal reaction mixture slurry was filtered, washed with deionized (DI) water and dried at 120° C. The as-synthesized material had an XRD patterns (FIG. 1) substantially as shown in Table I and Table II and only one peak (about 26.5°) between 26° to 29° (2θ). The resulting MCM-22 crystals had a $SiO_2/Al_2O_3$ molar ratio of ~23/1. The calcined MCM-22 crystals had a surface area of 653 m²/g (micropore surface area of 530 and external surface area of 123 m²/g). The SEM image (FIG. 5) of the as-synthesized product crystal showed a platelet morphology with an average crystal thickness of about 200 to about 300 Å. The estimate average platelet diameter was less than about 1 μm. The calcined material had a mesitylene uptake of about 29.8 mg/g and a mesitylene sorption rate of about 68 mg/g/min. The estimated yield of MCM-22 material (based on the dried weight of the molecular sieve product divided by the total weight of the hydrothermal reaction mixture) was about 11.7 wt. %. The weight hourly throughput was about 0.0019 hr⁻¹.

Examples 1-2

A hydrothermal reaction mixture were prepared from water, Hexamethyleneimine (HMI) (Sigma-Aldrich Company), silica (Ultrasil™, Degussa Corp.), 45 wt. % sodium aluminate solution, and 50 wt. % sodium hydroxide solution. The mixtures had the following molar compositions:

|  | Example 1 | Example 2 |
|---|---|---|
| Molar composition | | |
| $SiO_2/Al_2O_3$ | ~30 | 35 |
| $H_2O/SiO_2$ | ~13 | 14.6 |
| $OH^-/SiO_2$ | ~0.15 | 0.15 |
| $Na^+/SiO_2$ | ~0.15 | 0.15 |
| $HMI/SiO_2$ | ~0.2 | 0.2 |
| Solid-content (wt. %) | ~20 | 18 |
| Crystallization conditions | | |
| Temperature (° C.) | 170 | 180 |
| Stirring speed (RPM) | 250 | 350 |
| Time (hr) | 24 | 12 |
| Estimated Yield (wt. %) | ~16.7 | ~15.3 |
| XRD Result | MCM-22 | MCM-22 |
| Crystallinity (%) | 105 | 100 |
| $SiO_2/Al_2O_3$ (molar ratio) | ~24 | ~23 |
| Weight Hourly Throughput (hr⁻¹) | 0.0082 | 0.015 |
| Mesitylene uptake (mg/g) | 24.7 | |
| Mesitylene sorption rate (mg/g/min) | 45 | |

The mixture of example 1 was crystallized at 170° C. in an autoclave with stirring at 250 rotation per minute (RPM) for 24 hours. After crystallization, the hydrothermal reaction mixture slurry of example 1 was filtered, washed with deionized (DI) water and dried at 120° C. The as-synthesized material had an XRD patterns (FIG. 2) substantially as shown in Table I and Table II and an additional peak (26.9)° between 26.6° to 29° (2θ) as comparing to the example 1 (reference example). The resulting MCM-22 crystals had crystallinity of 105%, which is measured by the sum of the two main peaks (2θ at 7.1 and 26) to the sum of the same peaks in the example 1 (reference example). The resulting MCM-22 crystals had a $SiO_2/Al_2O_3$ molar ratio of ~24/1. The calcined MCM-22 crystals had a surface area of 612 m²/g (micropore surface area of 528 and external surface area of 84 m²/g). The SEM image (FIG. 6) of the as-synthesized product crystal showed a platelet morphology with an average crystal thickness of at least 300 Å, which is thicker than the reference example. The estimate average crystal thickness measured by SEM was about 300 Å to about 500 Å. The estimate average platelet diameter was less than about 1 μm, which is similar as the reference example. The calcined material had a mesitylene uptake of about 24.7 mg/g and a mesitylene sorption rate of about 45 mg/g/min. The estimated yield of MCM-22 material (based on the dried weight of the molecular sieve product divided by the total weight of the hydrothermal reaction mixture) was about 16.7 wt. %. The weight hourly throughput was about 0.0082 hr⁻¹. The weight hourly throughput of example 1 was about 525% of the comparative example.

The mixture of example 2 was crystallized at 180° C. in an autoclave with stirring at 350 rotation per minute (RPM) for 12 hours. After crystallization, the hydrothermal reaction mixture slurry of example 2 was filtered, washed with deionized (DI) water and dried at 120° C. The XRD patterns of the as-synthesized material showed the typical pure phase of MCM-22 topology. The resulting MCM-22 crystals had a $SiO_2/Al_2O_3$ molar ratio of ~23/1. The estimated yield of MCM-22 material (based on the dried weight of the molecular sieve product divided by the total weight of the hydrothermal reaction mixture) was about 15.3 wt. %. The weight hourly throughput was about 0.015 hr⁻¹. The weight hourly throughput of example 2 was about 780% of the comparative example.

Examples 3-4

Two mixtures were prepared from water, Hexamethyleneimine (HMI) (Sigma-Aldrich Company), silica (Ultrasil™, Degussa Corp.), 45 wt. % sodium aluminate solution, and 50 wt. % sodium hydroxide solution. The mixtures had the following molar composition:

| Example | Example 3 | Example 4 |
|---|---|---|
| Molar composition | | |
| $SiO_2/Al_2O_3$ | 25 | 30 |
| $H_2O/SiO_2$ | 13 | 12.81 |
| $OH^-/SiO_2$ | 0.15 | 0.175 |
| $Na^+/SiO_2$ | 0.15 | 0.175 |
| $HMI/SiO_2$ | 0.18 | 0.18 |
| Solid-content (wt. %) | ~20 | ~20 |
| Crystallization conditions | | |
| Temperature (° C.) | 170 | 170 |
| Stirring speed (RPM) | 250 | 250 |
| Time (hr) | 16, 18, 20, 22, 24 | 18, 20, 22 |
| Estimated Yield (wt. %) | ~17 | ~17 |
| XRD Result | MCM-22/MCM-49 | MCM-22/MCM-49 |
| Crystallinity (%) | 89, 91, 100, 100, 100 | 100, 100, 100 |
| $SiO_2/Al_2O_3$ (molar ratio) | | |
| Weight Hourly Throughput (hr⁻¹) | 0.01 | 0.011 |

The products were filtered, washed with deionized (DI) water and dried at 120° C. The XRD patterns of the as-synthesized materials (example 3) after 16, 18, 20, 22, and 24 hours showed MCM-22/MCM-49 topology with 89%, 91%, 100%, 100%, and 100% crystallinity. The XRD patterns of the as-synthesized materials after 18, 20, and 22 hours (example 4) showed the MCM-22/MCM-49 topology with 100% crystallinity. The estimated yields of MCM-22 material were about 17 wt. % for both examples. The weight hourly throughput were about 0.01 hr⁻¹ (example 3) and 0.011 (example 4). The weight hourly throughput of example 3 was about 520% of the comparative example. The weight hourly throughput of example 4 was about 580% of the comparative example.

Examples 5-7

Three mixtures were prepared from water, Hexamethyleneimine (HMI) (Sigma-Aldrich Company), silica (Ultrasil™, Degussa Corp.), 45 wt. % sodium aluminate solution, and 50 wt. % sodium hydroxide solution. The mixtures had the following molar compositions:

| Example | 5 | 6 | 7 |
|---|---|---|---|
| Molar composition | | | |
| $SiO_2/Al_2O_3$ | 35 | ~31.4 | ~31.5 |
| $H_2O/SiO_2$ | 12.65 | ~6.85 | ~12.7 |
| $OH^-/SiO_2$ | 0.175 | ~0.15 | ~0.15 |
| $Na^+/SiO_2$ | 0.175 | ~0.15 | ~0.15 |
| $HMI/SiO_2$ | 0.18 | ~0.2 | ~0.2 |
| Solid-content (wt. %) | ~20 | ~30 | ~20 |
| Crystallization conditions | | | |
| Temperature (° C.) | 170 | 170 | 205 |
| Stirring speed (RPM) | 250 | 60 | 250 |
| Time (hr) | 24 | 20 | 20 |
| Estimated Yield (wt. %) | ~17.1 | ~25.5 | ~17 |
| XRD Result | MCM-22 | MCM-22 | MCM-22 with ZSM-5 (<10%) |
| Crystallinity (%) | 100 | 100 | 100 |
| $SiO_2/Al_2O_3$ (molar ratio) | | 27.5 | 24 |
| Weight Hourly Throughput (hr⁻¹) | 0.008 | 0.015 | 0.01 |

The products were filtered, washed with deionized (DI) water and dried at 120° C. The XRD patterns of the as-synthesized material (example 5) showed the pure phase MCM-22 topology. The XRD patterns of the as-synthesized material (example 6) showed the pure phase of MCM-22 topology. The resulting MCM-22 crystals (example 6) had a $SiO_2/Al_2O_3$ molar ratio of 27.5. The XRD patterns of the as-synthesized material (example 7) showed the MCM-22 topology with ZSM-5 impurity. ZSM-5 impurity was estimated to be <10% in the resulting product. The resulting MCM-22 crystals (example 7) had a $SiO_2/Al_2O_3$ molar ratio of ~24. The estimated yields of MCM-22 material were about 17.1 wt. % (example 5), about 25.5 wt. % (example 6), and about 17 wt. % (example 7). The weight hourly throughput were about 0.008 hr⁻¹ (example 5), 0.015 hr⁻¹ (example 6), and 0.01 (example 7). The weight hourly throughputs were about 440% (example 5), about 780% (example 6), and about 520% (example 7) of the comparative example.

Example 8

A MCM-22/alumina catalyst was prepared from 80 weight parts of product of Example 5 mixed with 20 weight parts of alumina (LaRoche Versal 300) on the dry basis. Water was added to the mixture to allow the resulting catalyst to be formed into extrudates. The prepared extrudates were dried at 120° C. before use. The catalyst was activated by calcining in nitrogen at 540° C., followed by aqueous ammonium nitrate exchange and calcining in air at 540° C.

Example 9

The catalyst prepared in Example 8 is tested for benzene alkylation with propylene in a 300 ml autoclave. The finished catalyst was transferred into the catalyst basket and then dried in an oven at 260° C. for about 16 hours. This catalyst basket was then transferred into a 300 ml autoclave quickly with minimum exposure to ambient atmosphere. The catalyst was then purged with dry nitrogen for 2 hours at 181° C. inside the reactor to removed air and moisture from the reactor. One hundred fifty six grams of benzene was transferred to the reactor under nitrogen and equilibrated with the catalyst for 1 hour at 130° C. Twenty eight grams of propylene was transferred into reactor under 2170 KPa-a of nitrogen pressure.

The reaction started as soon as propylene was added and a constant pressure of 2170 KPa-a nitrogen blanketed the autoclave. The reaction was allowed to run for four hours and propylene was completely consumed during this period. Small samples of liquid were withdrawn from the autoclave at regular interval for analysis of propylene, benzene, cumene (IPB), diisopropylbenzene(s) (DIPB), and triisopropylbenzene(s) (TIPB), using gas chromatography. Catalyst performance was assessed by a kinetic activity rate parameter base on propylene and benzene conversion. Cumene selectivity was calculated from the weight ratio of DIPB/cumene (expressed as percentage). The calculation method was as referenced in WO 03/006160. The results were as shown in the following table.

| Catalyst | Activity | Selectivity DIPB/Cumene (%) |
|---|---|---|
| Example 8 | 370 | 13 |

The catalyst showed both activity and selectivity for benzene alkylation reaction.

While the illustrative embodiments of this invention have been described with particularity, it will be understood that various other modifications will be apparent to and can be readily made by those skilled in the art without departing from the spirit and scope of this invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

We claim:

1. A molecular sieve manufactured by a method comprising the steps of:
(a) providing a mixture comprising at least one source of ions of a tetravalent element, at least one source of an alkali metal hydroxide, at least one directing-agent (R), water, and optionally at least one source of ions of a trivalent element, said mixture having the following mole composition:
$Y:X_2$=10 to infinity
$H_2O:Y$=1 to 20
$OH^-:Y$=0.001 to 2
$M^+:Y$=0.001 to 2
$R:Y$=0.001 to 0.34
wherein Y is a tetravalent element, X is a trivalent element, M is an alkali metal;
(b) treating said mixture to form said molecular sieve at crystallization conditions, wherein said crystallization conditions comprise a temperature in the range of from about 165° C. to about 250° C., and crystallization time less than 72 hr; and
(c) recovering said molecular sieve,
wherein said molecular sieve is characterized by an X-ray diffraction pattern including d-spacing maxima at 12.4±0.25, 3.57±0.07 and 3.42±0.07 Angstroms and at least one peak between 26.6° and 29° (2θ).

2. The molecular sieve recited in claim 1, wherein said X-ray diffraction peak between 26.6° and 29° (2θ) has a two theta (2θ) value of about 26.9°.

3. The molecular sieve recited in claim 1, wherein said molecular sieve has a platelet morphology having a crystal thickness at least 300 Å measured by SEM.

4. A hydrocarbon conversion process, said process comprising the steps of:
(a) contacting a hydrocarbon feedstock with a molecular sieve of the MCM-22 family recited in claim 1 under conversion conditions to form a product; and
(b) withdrawing said product.

5. The process of claim 4, wherein said hydrocarbon feedstock comprises at least one of $C_1$-$C_{20}$ hydrocarbons and $C_1$-$C_{20}$ oxygenates.

6. The process of claim 4, wherein said conversion conditions comprise a temperature ranging from about 100° C. to 950° C., a pressure ranging from about 101 kPa-a to 50000 kPa-a, and a WHSV ranging from about 0.001 to 1000 $hr^{-1}$.

7. The process of claim 4, wherein said hydrocarbon conversion process is a process for the alkylation of benzene with ethylene to form ethylbenzene, and hydrocarbon feedstock comprises benzene and ethylene.

8. The process of claim 4, wherein said hydrocarbon conversion process is a process for the alkylation of benzene with propylene to form cumene, and hydrocarbon feedstock comprises benzene and ethylene.

* * * * *